United States Patent [19]

Jones

[11] 4,008,238
[45] Feb. 15, 1977

[54] 24-METHYL-14A-AZA-D-HOMO-CHOLESTADIENE DERIVATIVES

[75] Inventor: Charles D. Jones, Indianapolis, Ind.

[73] Assignee: Eli Lilly and Company, Indianapolis, Ind.

[22] Filed: Jan. 29, 1976

[21] Appl. No.: 653,676

Related U.S. Application Data

[63] Continuation-in-part of Ser. No. 503,563, Sept. 6, 1974, abandoned.

[52] U.S. Cl. .................. 260/289 AZ; 260/287 AZ; 424/258
[51] Int. Cl.$^2$ ...................... C07D 215/16
[58] Field of Search ............................ 260/289 AZ

[56] References Cited

UNITED STATES PATENTS

| | | | |
|---|---|---|---|
| 2,738,350 | 1/1956 | Mazur | 260/289 R |
| 3,845,203 | 10/1974 | Williams et al. | 424/122 |

OTHER PUBLICATIONS

Tsuda et al., J. Am. Chem. Soc., vol. 78, pp. 4107–4111 (1956).

*Primary Examiner*—Donald G. Daus
*Assistant Examiner*—David B. Springer
*Attorney, Agent, or Firm*—Charles W. Ashbrook; Everet F. Smith

[57] ABSTRACT

Addition to the exo-methylene group of 24-methylene-14a-aza-D-homo-cholesta-8(9), 14(14a)-dienes provides novel aza-steroids having antifungal activities.

9 Claims, No Drawings

24-METHYL-14A-AZA-D-HOMO-CHOLESTADIENE DERIVATIVES

CROSS-REFERENCE TO RELATED APPLICATIONS

This application is a continuation-in-part of copending application Ser. No. 503,563, filed Sept. 6, 1974, now abandoned.

BACKGROUND OF THE INVENTION

Infections having fungal origins constitute a large portion of human diseases caused by microorganisms. Several naturally occurring antibiotics and numerous synthetic compounds are currently available for treating fungal infections. Nystatin, a polyene antibiotic whose structural formula is not yet fully elucidated, is a commonly used antifungal agent which has met with good success. Even with the currently available antifungal agents however, there are still several diseases of fungal origin which are not easily controllable. Additionally, certain antifungal agents become ineffective with continued use due to the patient's sensitization to the particular drug. Consequently, the search for new antifungal agents and the therapy of fungal infections is the object of much laboratory and clinical investigation.

The isolation and characterization of novel 24-methylene-14a-aza-D-homo-cholestadines which show good antifungal activity has recently been accomplished from cultures of a strain of Geotrichum flavobrunneum. This organism is described in detail by Miller et al., Mycologia 49, 779–808, 1957. The preparation and isolation of these noval azasteroids is the subject of U.S. Pat. No. 3,845,203.

The compounds provided by the present invention are in general prepared by modifying the side chain portion of the above-mentioned naturally occurring 24-methylene-14a-aza-D-homo-cholestadines. The compounds provided herein are useful as antifungal agents.

SUMMARY OF THE INVENTION

The compounds of this invention have the formula:

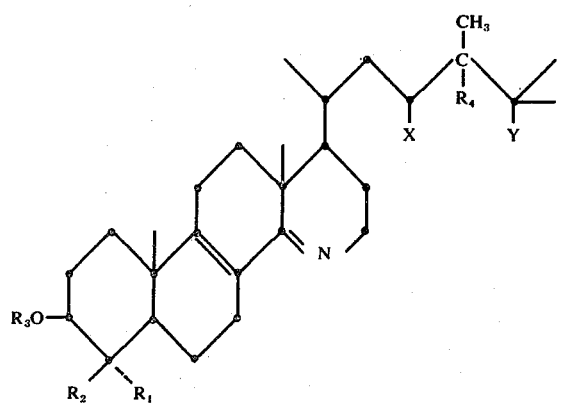

in which $R_1$ and $R_2$ are both hydrogen or both methyl; $R_3$ is hydrogen or $C_1-C_4$ alkanoyl; $R_4$ is hydroxy or halogen, and X and Y are both hydrogen, or when taken together, $R_4$ and X form a double bond or $R_4$ and Y form a double bond. Included within the breadth of this invention are the pharmaceutically acceptable salts of the organic bases of the invention.

DETAILED DESCRIPTION OF THE INVENTION

The compounds of this invention are 24-methyl-14a-aza-D-homo-cholestadiene derivatives having the above general formula.

As used herein, the term "$C_1-C_4$ alkanoyl" refers to carboxylic acid residues such as formyl, acetyl, propionyl, butyryl, and isobutyryl. The term "halo" includes fluoro, chloro, bromo, and iodo.

The organic bases of this invention generally form pharmaceutically acceptable salts with a variety of inorganic and organic acids. While the particular acid used in salt formation is not of a critical nature, the corresponding salt that is formed should be substantially non-toxic to animal organisms. Examples of acids commonly used in salt formation include hydrochloric, hydrobromic, hydroiodic, sulfuric, phosphoric, sulfamic, acetic, succinic, benzoic, ascorbic, citric, maleic, and related acids. Additionally, the organic bases of the invention form quaternary immonium salts with any of a number of alkylating agents, including methyl iodide, ethyl bromide, allyl chloride, methyl sulfate, ethyl toluenesulfonate, and the like. The compounds of this invention are generally prepared by acidic addition to the exo-methylene group of a naturally occurring steroid-like substance having the formula:

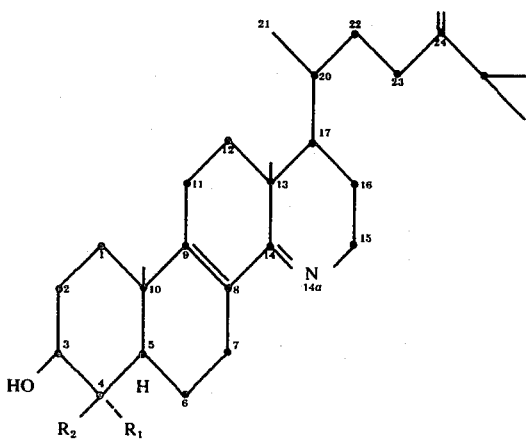

in which $R_1$ and $R_2$ are both hydrogen or both methyl. The compounds of this invention are systematically named by following the standard steroid nomenclature system and by referring to the numbering system shown in the above formula. A typical starting material, for example, is named 3β-hydroxy-24-methylene-14a-aza-D-homo-5α-cholesta-8(9), 14(14a)-diene. All of the new compounds provided by this invention will have the same stereochemical configuration as the starting material, except at the site of reaction. For example, all of the new compounds disclosed herein will have a 3β-hydroxyl or alkanoyloxyl group, as evidenced in the above formual by the solid bonding line between the $C_3$ carbon-oxygen atoms. Similarly, the compounds of this invention all have a 5α-hydrogen atom. Consequently, the nomenclature used herein will be simplified throughout this application by omitting the stereochemical designations of α and β. As an example, the above-named starting material will hereinafter be named 3-hydroxy-24-methylene-14a-aza-D-homo-cholesta-8(9), 14(14a)-diene.

According to this invention, the 24-methylene-14a-aza-D-homo-cholestadiene starting material is treated with a hydrogen halide, thereby converting the 24-methylene group into a 24-methyl-24-halo group. In particular, the 24-methylene-14a-aza-D-homo steroid is commingled with an excess amount of a mineral acid of the hydrohalide type, generally in an organic solvent. The acid used is preferably one that is substantially free of water, such as gaseous hydrogen chloride or gaseous hydrogen bromide for example. The amount of acid used is normally not critical, and the reaction solution is customarily simply saturated with such a gaseous acid. Typical solvents commonly employed for the reaction include halogenated hydrocarbons such as chloroform of dichloromethane, or aromatic solvents such as benzene or toluene for example. The reaction is substantially complete after about 2 to 6 hours when carried out at a temperature of about 40° to 80° C. The product is isolated be removal of the solvent to provide the product as the immonium halide salt, which can be converted to the free base when desired by the addition of a suitable base, such as sodium hydroxide or the like. The product, either as the free base or as the acid addition salt, can be further purified if desired by crystallization, chromatography, or similar methods. It will be understood that a new asymmetric center has been created by the addition of a hydrogen halide across the 24-methylene unsaturation, thus giving a mixture of isomers as the product. Generally, the compounds are used without separation of the stereoisomers.

An additional aspect of the invention is the addition of water across the 24-methylene unsaturation to provide a 24-methyl-24-hydroxy-aza-D-homo-steroid. In particular, the 24-methylene-14a-aza-D-homo-cholesta-8(9), 14(14a)-diene is reacted with an aqueous acid, such as aqueous perchloric acid for example, normally in a solvent such as an alcohol or an ether, for example methanol or dioxane. The reaction is generally carried out at an elevated temperature, from about 40° to about 60° C. for instance. The reaction is substantially complete after about 2 to about 8 hours, and the product is isolated by removal of the solvent. Further purification, such as chromatography, can be carried out if desired, but generally is not required. Alternatively, the product can be isolated as an addition salt which is typically a crystalline solid and can be further purified by recrystallization if desired. For example, the 24-methyl-24-hydroxy derivative can be treated with a suitable acid, such as gaseous hydrogen bromide for instance, in a solvent such as diethyl ether. The corresponding acid addition salt generally precipitates out of solution and can be collected by filtration.

The 24-methyl-24-halo-14a-aza-D-homo-cholestadienes prepared as described hereinabove are especially useful in controlling fungal infections, and additionally these compounds serve as intermediates leading to still other antifungal agents. For example, these 24-methyl-24-halo-14a-aza-D-homo-cholestadiene derivatives can be dehydrohalogenated to provide the corresponding new 23,24-dehydro compounds and the 24,25-dehydro compounds. The dehydrohalogenation reactions are generally carried out by treating the compound of the above formula, wherein $R_4$ is halogen, with a base, normally in a suitable solvent. Preferred bases are the alkali metal hydroxides, such as sodium or potassium hydroxide for example. Typical solvents include alcohols such as methanol or ethanol, and water. The reaction is generally carried out at a temperature of about 25° to 100° C., and is substantially complete after about 2 to 6 hours. The product is isolated by removal of the solvent. The product is a mixture of the 23,24-dehydro, 24,25-dehydro and the 24-methylene compounds. The mixture of dehydro compounds is most conveniently used to treat fungal infections, however, some separation can be achieved with purification techniques such as high pressure liquid chromatography, gas chromatography, and the like.

Alternatively, the 24-methylene-14a-aza-D-homo-cholesta-8(9), 14(14a)-dienes can be converted to the corresponding 23,24-dehydro and 24,-25dehydro derivatives by reaction with a suitable acid, generally in an organic solvent. More particularly, the 24-exo methylene unsaturation can be isomerized by treatment with acids such as toluenesulfonic acid, trifluoroacetic acid, chlorosulfonic acid, sulfuric acid, and the like. The reaction is normally carried out in a solvent such as benzene and toluene, and preferably at a temperature of about 30° to about 80° C. The reaction is generally complete after about 12 to 24 hours, and the product is recovered by removal of the solvent. The product, a mixture of 23,24-dehydro and 24,25-dehydro derivatives, is typically used to combat fungal growth without further purification.

It should be further noted that the $C_8$–$C_9$ double bond and the $C_{14}$–$N_{14a}$ double bond of the 24-methylene-14a-aza-D-homo-cholestadiene can be reduced to provide additional new antifungal agents. In particular, the $C_8$–$C_9$ unsaturation can be selectively reduced in preference to the $C_{14}$–$N_{14a}$ unsaturation by employing dissolving metal reduction conditions, such as sodium in liquid ammonia for example. Similarly, the $C_{14}$–$N_{14a}$ unsaturation can be selectively reduced by employing an agent such as sodium borohydride.

Illustrative examples of compounds provided by this invention include:

3-Hydroxy-24-methyl-24-hydroxy-14a-aza-D-homo-cholesta-8(9), 14(14a)-diene;

3-Hydroxy-4,4,24-trimethyl-24-chloro-14a-aza-D-homo-cholesta-8(9), 14(14a)-diene;

3Acetoxy-4,4,24-trimethyl-24-chloro-14a-aza-D-homo-cholesta-8(9), 14(14a)-diene;

3-Hydroxy-24-methyl-14a-aza-D-homo-cholesta-8(9), 14 (–a), 23(24)-triene;

3-Hydroxy-4,4,24-trimethyl-24-bromo-14a-aza-D-homo-cholesta-8(9), 14(14a)-diene-14a-ium bromide;

3-Hydroxy-24-methyl-24-iodo-14a-aza-D-homo-cholesta-8(9), 14(14a)-diene-14a-ium acetate;

3-Isobutyroxy-14a,24-dimethyl-24-hydroxy-14a-azonia-D-homo-cholesta-8(9), 14(14a)-diene iodide;

3-Hydroxy-24-methyl-24-fluoro-14a-aza-D-homo-cholesta-8(9), 14(14a)-dienes and are obtained by culturing a strain of *Geotrichum flavo-brunneum*, NRRL 3862, which strain is in the permanent culture collection of the Agricultural Research Service, Northern utilization Research and Development Division, Department of Agriculture, Peoria, Illinois. The organism which is cultured was isolated by the standard serial dilution procedure from a soil sample collected in the Grand Teton National Park region of Wyoming. The organism is described in detail by Miller, et al., *Mycologia*, 49, 779-808, 1957. The preparation and isolation of the starting material used in the present invention is the subject of U.S. Pat. No. 3,845,203, and is carried out as described hereinbelow.

A culture of *Geotrichum flavo-brunneum* is grown under submerged aerobic conditions in a fermentation medium comprising carbohydrates, amino acids, and nutrient inorganic salts. The organism is grown for about 3 days at a temperature of about 20° to 35° C. After the fermentation is complete, the fermentation mycelium is extracted with a suitable organic solvent, such as ethyl acetate or amyl acetate for instance. Evaporation of the solvent from the combined organic extracts provides a mixture of compounds. The starting materials for the present invention are separated from the mixture by chromatography and crystallization.

The new compounds of the present invention are useful chemotherapeutic agents, particularly because of their antifungal properties against microorganisms such as *Candida tropicalis*, *Candida albicans*, and *Trichophyton mentagraphytes*. For example, when tested in a standard disc plate assay, 3-hydroxy-24-methyl-24-chloro-14a-aza-D-homocholesta-8(9), 14(14a)-diene demonstrated a minimum inhibitory concentration (MIC) of 0.312 µg/ml against *C. albicans* and 0.0625 µg/ml against *T. mentagraphytes*. Similarly, 3-formyloxy-24-methyl-14a-aza-D-homo-cholesta-8(9), 14(14a), 24(25)-triene demonstrated an MIC of 0.25 µg/ml. against *C. albicans* and 0.0312 µg/ml. against *T. mentagraphytes*. Additionally, 3-hydroxy-24-methyl-24-hydroxy-14a-aza-D-homo-cholesta-8(9), 14(14a)-diene displayed an MIC of 0.625 µg/ml. against *C. albicans* and 0.125 µg/ml. against T. *mentagraphytes*.

The compounds of this invention inhibit fungal growth when applied to environmental surfaces such as shower stalls, foot baths, exterior surfaces of wood, concrete, brick, or the like, as well as to skin surfaces affected by fungal growth. The compounds are most conveniently formulated with a suitable diluent, excipient, or carrier for use as a solution, spray, elixir, powder or suspension. Typical diluents and carriers include water, ethanol, propylene glycol, mannitol, glycerol and the like. Additionally, the compound can be formulated as a cream or ointment with suitable carriers such as hydrocarbon waxes, polyethylene glycol, lanolin, vegetable oils or a cold cream base, thereby being suitably formulated for topical application to infected skin surfaces. As an example, an antifungal agent provided by this invention, such as 3-hydroxy-24-methyl-24-bromo-14a-aza-D-homo-cholesta-8(9), 14(14a)-diene hydrobromide, can be formulated by dissolving from about 0.5 to about 5 grams of such compound in about 1000 ml. of water. Such solution can be applied to a surface such as a foot bath or shower stall to control fungal growth on such surface. An ointment can be prepared by combining about 250 mg. of a compound of this invention, for instance 3-acetoxy-24-methyl-14a-aza-D-homo-cholesta-8(9), 14(14a), 24(25)-triene, with about 500 mg. of propylene glycol and about 500 mg. of lanolin. Such formulation can be applied to a mammal's skin surface which is infected with a fungus in order to control such fungal infection. Such application will be made in accordance with the particular condition being treated; but will generally be made so as to apply from about 0.1 to 5 mg. of active ingredient per square centimeter of infected skin surface.

The preparation of typical compounds provided herein is more fully described in the following detailed perparations and examples. It is to be understood, however, that the examples are provided to serve only as illustration of particular aspects of the invention, and are not to be construed as limiting the invention to the compounds or methods specifically described. The compounds described hereinbelow are characterized by mass spectral (m/e) parent molecular ion absorption ($M^+$), and by melting point.

Preparation 1

The production of the starting materials required for the present invention is illustrated by the following procedures.

Spores of *Geotrichum flavo-brunneum* strain NRRL 3862 were inoculated on a nutrient agar slant having the following composition:

| Agar Slant Medium | |
|---|---|
| Ingredient | Weight/Volume (g./l.) |
| Glucose | 20 |
| Peptone | 5 |
| Potassium Dihydrogen Phosphate | 0.5 |
| Magnesium Sulfate | 0.02 |
| Ferrous Sulfate | 0.01 |
| Agar | 20 |

The above cultures were incubted at a temperature of 25° C. for 7 days. A loop of spores from the slant culture was transferred to a vegetative inoculum having the following composition:

| Vegetative Medium | |
|---|---|
| Ingredient | Weight/Volume (g./l.) |
| Sucrose | 25 |
| Edible Molasses | 36 |
| Corn Steep | 6 |
| Potassium Dihydrogen Phosphate | 2 |
| NZ Case[1] | 2 |
| Tap Water | |

[1]Enzymatic digest of casein, Scheffield Chemical Co., Norwich, N.Y.

The inoculated vegetative medium was shaken on a rotary shaker at 250 r.p.m. for about 24 to 48 hours at a temperature of about 25° C. Five percent of the volume of the vegetative inoculum containing viable vegetative growth was employed to inoculate a fermentation medium having the following composition:

| Fermentation Medium | |
|---|---|
| Ingredient | Weight/Volume (g./l.) |
| Glucose | 25 |
| Corn Starch | 10 |
| Peptone (meat) | 10 |
| NZ Amine A[1] | 4 |
| Molasses | 5 |
| Magnesium Sulfate Heptahydrate | 5 |
| Calcium Carbonate | 2 |
| Tap Water | |

[1]Pancreatic hydrolysate of casein, Scheffield Chemical Company, Norwich, N.Y.

The inoculated fermentation medium was agitated continuously for 72 hours at a temperature 25° C. Throughout the fermentation, sterile air was passed through the fermentation medium at a rate of one half volume of air per volume of fermentation medium per minute.

Upon completion of the fermentation, the fermentation broth was extracted several times ethyl acetate. The combined ethyl acetate extracts were concentrated to an oil residue. The residue was dissolved in a 20 percent acetone solution in n-hexane. Additional hexane was added to the mixture, and the solution was cooled to −20° C. whereupon 3-hydroxy-24-methylene-14a-aza-D-homo-cholesta-8(9), 14(14a)-diene crystallized. The crystals were collected by filtration and air dried, m.p. 115°–118° C. The filtrate was concentrated to dryness, providing oily residue which was dissolved in a mixture of ethyl acetate-hexane-distilled water (80:16:4). The solution was passed over a column packed with basic alumina (Wolem grade W200, Water Associates, Inc., Framingham, Mass.). The column was eluted with the same solvent mixture, and eluate fractions of 1 liter volume each were collected. Elutate fractions 9 through 23 were combined and the solvent was removed therefrom under reduced pressure to provide a residue which was crystallized from acetone. The crystals were collected by filtration and identified as 3-hydroxy-24-methylene-14a-aza-D-homo-4,4-dimethyl-cholesta-8(9), 14(14a)-diene, m.p. 147° C.

EXAMPLE 1

3-hydroxy-24-methyl-24-chloro-14a-aza-D-homo-cholesta-8(9), 14(14a)-diene hydrochloride A solution of 1 g. of 3-hydroxy-24-methylene-14a-aza-D-homo-cholesta-8(9), 14(14a)-diene in 150 cc. of chloroform was stirred at 25° C. while gaseous hydrogen chloride was added until the solution was saturated. The reaction mixture was heated at 55°–60° c. for 4 hours. After cooling the reaction mixture to about 25° C., the solvent was removed under reduced pressure, affording 1.16 g. of 3-hydroxy-24-methyl-24-chloro-14a-aza-D-homo-cholesta-8(9), 14(14a)-diene hydrochloride. M.P. 115°–120° C.

EXAMPLE 2

3-Hydroxy-24-methyl-24-hydroxy-14a-aza-D-homo-cholesta-8(9), 14(14a)-diene

A solution of 200 mg. of 3-hydroxy-24-methylene-14a-aza-D-homo-cholesta-8(9), 14(14a)-diene in 10 cc. of methanol containing 10 cc. of 70 percent aqueous perchloric acid was heted at 50° C. for 4 hours. The solvent was removed under reduced pressure and aqueous sodium bicarbonate was added to the reaction mixture and the product was extracted therefrom with ethyl acetate. The organic extract was dried and the solvent was removed under reduced pressure to provide 180 mg. of 3-hydroxy-24-methyl-24-hydroxy-14a-aza-D-homo-cholesta-8(9), 14(14a)-diene as an oil. m/e: M+429.

EXAMPLE 3

3-Hydroxy-24-methyl-14a-aza-D-homo-cholesta-8(9), 14(14a), 23,(24)-triene and
3-Hydroxy-24-methyl-14a-aza-D-homol-cholesta-8(9), 14(14a), 24,(25)-triene A solution of 200 mg. of 3-hydroxy-24-methylene-14a-aza-D-homo-cholesta-8(9), 14(14a)-diene in 30 cc. of benzene was heated at reflux for 18 hours with 153 mg. of para-toluene-sulfonic acid mono-hydrate. The reaction flask was equipped with a thimble of 4A molecular sieves in order to dry the reaction mixture. Upon completion of the reaction, the solvent was removed under reduced pressure to provide a residue which was then dissolved in ethyl acetate. The organic solution was washed with aqueous sodium bicarbonate solution, dried, and the solvent was removed under reduced pressure, affording 200 mg. of a yellow oil. Proton magnetic resonance spectroscopy revealed a mixture comprised of about 35 percent of 3-hydroxy-24-methyl-14a-aza-D-homo-cholesta-8(9), 14(14a), 23(24)-triene and about 65 percent of 3-hydroxy-24-methyl-14a-aza-D-homo-cholesta-8(9), 14(14a), 24(25)-triene.

EXAMPLE 4

3-Formylxoy-24-methyl-14a-aza-D-homo-cholesta-8(9), 14(14a), 24(25)-triene

A solution of 1.0 g. of 3-hydroxy-24-methylene-14a-aza-D-homo-cholesta-8(9), 14(14a)-diene was dissolved in 35 ml. of 98 percent formic acid. The reaction mixture was heated at 50° C. for 5 hours. The reaction mixture was then concentrated by evaporation of the solvent under reduced pressure, providing an oil which was next dissolved in 50 ml. of ethylacetate. The solution was washed with 50 ml. of saturated aqueous sodium bicarbonate solution, water, dried, and concentrated to dryness by evaporation under reduced pressure to afford 1.0 g. of 3-formylozy-24-methyl-14a-aza-D-homo-cholesta-8(9), 14(14a), 24(25)-triene.

EXAMPLE 5

3-hydroxy-24-methyl-14-a-aza-D-homo-cholesta-8(9), 14(14a), 24(25)-triene.

A solution of 1.0 g. of 3-formyloxy-24-methyl-14a-aza-D-homo-cholesta-8(9),14(14a), 24(25)-tiene in 25 ml. of methanol containing 3.5 ml. of 1 N sodium hydroxide was stirred at 25° C. for 16 hours. The reaction mixture was concentrated by evaporation of the solvent under reduced pressure to provide an oil, and the oil so formed was dissolved in 50 ml. of ethyl acetate, washed with water and dried. Evaporation of the solvent under reduced pressure afforded 880 mg. of 3-hydroxy-24-methyl-14a-aza-D-homocholesta-8(9), 14(14a), 24(25)-triene.

I claim:
1. A compound of the formula

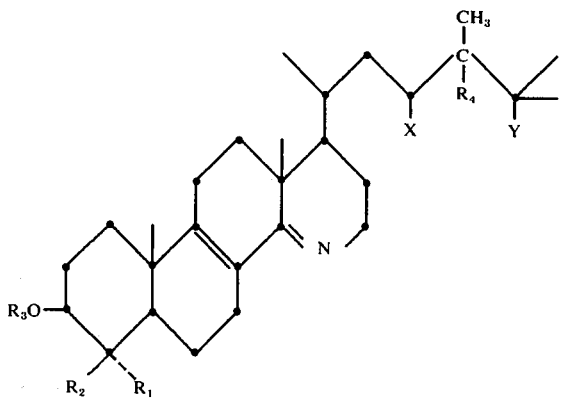

wherein:
$R_1$ and $R_2$ are both hydrogen or both methyl;
$R_3$ is hydrogen;

$R_4$ is halogen or hydroxyl, or when taken together with X or with Y forms a double bond;

X is hydrogen, or together with $R_4$ forms a double bond;

Y is hydrogen, or together with $R_4$ forms a double bond;

and the pharmaceutically acceptable salts thereof.

2. The compound of claim 1 wherein $R_1$ and $R_2$ are both hydrogen.

3. The compound of claim 2 wherein $R_3$ is hydrogen.

4. The compound of claim 3 wherein $R_4$ is halo.

5. The compound of claim 4 wherein $R_4$ is chloro.

6. The compound of claim 4 wherein $R_4$ is bromo.

7. The compound of claim 3 wherein $R_4$ is hydroxyl.

8. The compound of claim 3 wherein $R_4$ and X taken together form a double bond.

9. The compound of claim 3 wherein $R_4$ and Y taken together form a double bond.

* * * * *